(12) United States Patent
Carrel et al.

(10) Patent No.: US 8,075,535 B2
(45) Date of Patent: Dec. 13, 2011

(54) PRE-FILLED SYRINGE WITH ANTI-TAMPER CAP

(75) Inventors: Franck Carrel, Le Pont de Claix (FR); Frederic Perot, Saint Paul de Varces (FR); Laurent Barrelle, Saint Nizier du Moucherotte (FR)

(73) Assignee: Becton Dickinson France S.A., Le Pont de Claix (FR)

( * ) Notice: Subject to any disclaimer, the term of this patent is extended or adjusted under 35 U.S.C. 154(b) by 376 days.

(21) Appl. No.: 10/556,617

(22) PCT Filed: May 25, 2004

(86) PCT No.: PCT/FR2004/001294
§ 371 (c)(1),
(2), (4) Date: Mar. 19, 2007

(87) PCT Pub. No.: WO2004/105840
PCT Pub. Date: Dec. 9, 2004

(65) Prior Publication Data
US 2007/0250017 A1    Oct. 25, 2007

(30) Foreign Application Priority Data
May 26, 2003 (FR) ...................................... 03 06334

(51) Int. Cl.
*A61M 5/315* (2006.01)
(52) U.S. Cl. ...................................................... 604/220
(58) Field of Classification Search .................. 604/111, 604/199, 220, 227, 232, 110, 218
See application file for complete search history.

(56) References Cited

U.S. PATENT DOCUMENTS

| | | | | | |
|---|---|---|---|---|---|
| 3,306,290 | A | * | 2/1967 | Weltman | 604/197 |
| 4,531,940 | A | * | 7/1985 | Butterfield | 604/111 |
| 4,592,746 | A | * | 6/1986 | Burkholder et al. | 604/220 |
| 4,711,637 | A | * | 12/1987 | Leigh et al. | 604/220 |
| 5,700,247 | A | * | 12/1997 | Grimard et al. | 604/220 |
| 5,897,532 | A | * | 4/1999 | Spallek et al. | 604/187 |
| 5,925,032 | A | * | 7/1999 | Clements | 606/1 |
| 6,821,266 | B2 | * | 11/2004 | Knepshield et al. | 604/110 |
| 7,223,259 | B2 | * | 5/2007 | Marshall et al. | 604/198 |
| 2004/0158202 | A1 | * | 8/2004 | Jensen | 604/93.01 |

* cited by examiner

*Primary Examiner* — Kevin C Sirmons
*Assistant Examiner* — Kami A Bosworth
(74) *Attorney, Agent, or Firm* — Cozen O'Connor

(57) ABSTRACT

A prefilled ready-to-use syringe, including a tubular body having, at its distal end, a tip to take a needle and, at its proximal end, a flange, a piston able to slide inside the tubular body and defining, with the tubular body, an internal working volume at least partially filled with a liquid, a rod for actuating the piston extending beyond the proximal end of the tubular body, characterized in that a rigid cover is attached and fixed in a definitive way to the flange and has a central opening for the free translational passage of the actuating rod, and the said cover forms a stop for the actuating rod in the proximal direction, and a plug is arranged to translate freely in the tubular body between the piston and the proximal end of the body, the plug being resistant to puncturing with a needle.

7 Claims, 4 Drawing Sheets

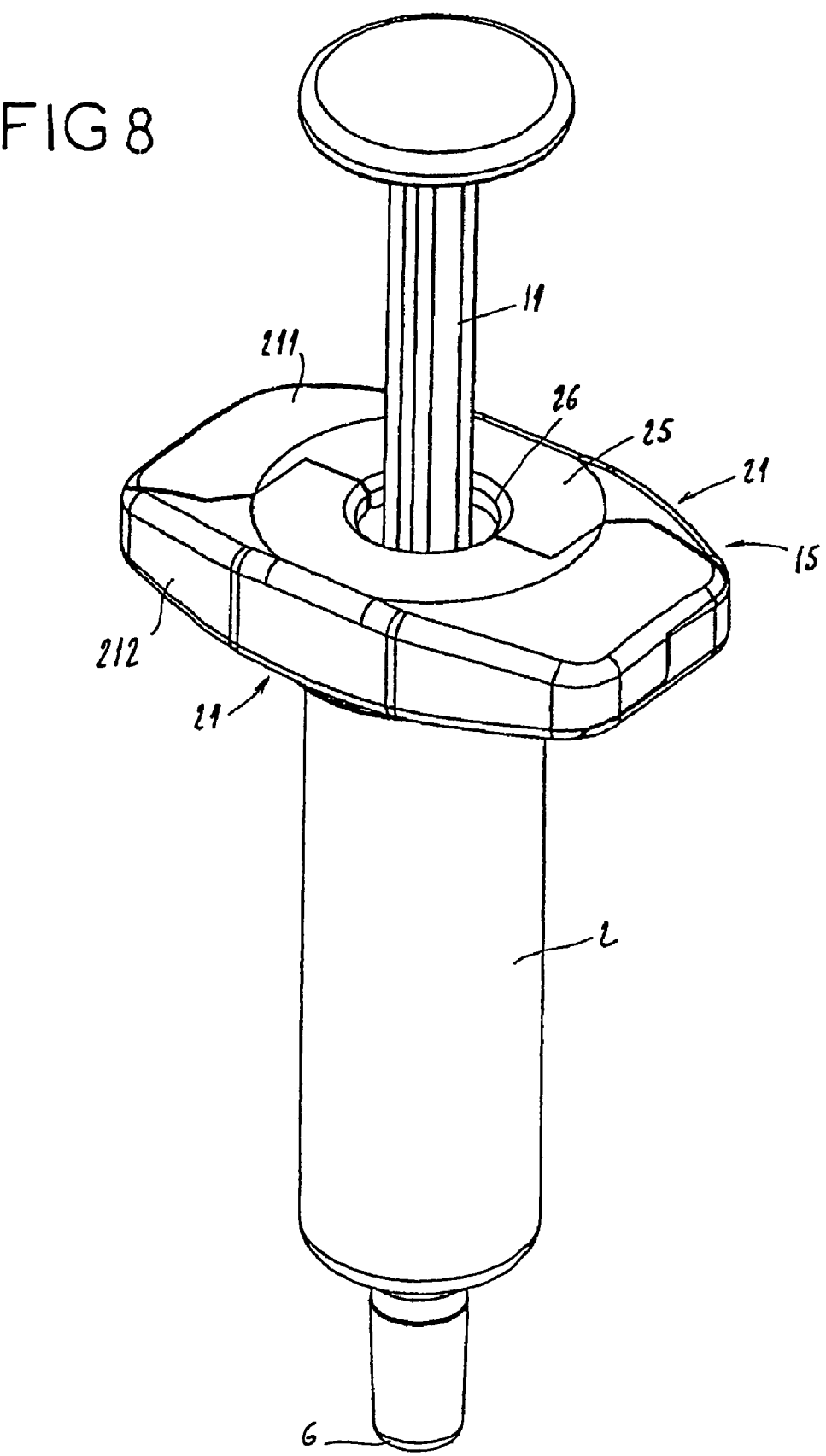

PRE-FILLED SYRINGE WITH ANTI-TAMPER CAP

CROSS-REFERENCE TO RELATED APPLICATIONS

This application is a national stage filing under 35 U.S.C. 371 of International Application No. PCT/FR04/01294, filed May 25, 2004, which claims priority from French Patent Application No. 03/06334 filed May 26, 2003 each of which is hereby incorporated by reference in its entirety.

FIELD OF THE INVENTION

The present invention relates to a device for medical use, of the prefilled syringe type comprising a piston, the said device comprising means for preventing access to the piston and its withdrawal once the said device has been filled with a medicinal liquid for example.

BACKGROUND OF THE INVENTION

In the field of prefilled ready-to-use syringes, devices have already been described that make it possible to determine whether or not the syringe has already been used. These devices generally relate to the distal end of the syringe, that is to say to the needle end of the syringe. Thus it has been proposed for the needle to be covered with a cap that has to be broken before the syringe can be used.

However, in the case of prefilled syringes, it is useful to provide a device preventing access to the piston. It is also useful to provide a device preventing the piston from being withdrawn. This is because it can happen that the actuating rod that actuates the piston is removed and the piston is then punctured with a needle to inject into the syringe a liquid or component that is unforeseen or unauthorized. The rod is then refitted to the piston.

During the process of manufacture of this type of syringe, the syringes are filled in a sterile environment then packaged and possibly sterilized. It is between these two steps of filling and packaging that the internal chamber of these syringes must not be exposed or that the drug it contains must not be contaminated.

Document EP 0 738 517 describes an open clip that is slipped, while the piston actuating rod is already mounted, over the flange situated on the proximal part of the body of the syringe so as to prevent movement and/or withdrawal of the syringe piston. However, this clip, because it is open, can easily be removed and then reinstated on the flange of the syringe. It cannot therefore be used to deny access to the piston. Nor does it prevent withdrawal of the piston.

Other systems said to be "closed" exist, but the withdrawal of the piston is prevented only when the piston actuating rod is present.

SUMMARY OF THE INVENTION

The present invention aims to remedy this problem by proposing a prefilled syringe equipped with a means making it possible both to prevent access to the piston and to prevent the piston from being withdrawn.

The present invention relates to a device for medical use, of the prefilled ready-to-use syringe type, comprising a tubular body comprising, at its distal end, a tip to take a needle and, at its proximal end, a flange, a piston able to slide inside the tubular body and arranged in an initial position defining, with the tubular body, an internal working volume at least partially filled with a medicinal liquid, a rod for actuating the piston extending beyond the proximal end of the tubular body, characterized in that a rigid cover is attached and fixed in a definitive way to the flange and has a central opening for the free translational passage of the actuating rod, and the said cover forms or comprises means of stopping the actuating rod in the proximal direction, and in that a plug is arranged to translate freely in the tubular body between the piston and the proximal end of the said body, said plug being made of a material resistant to puncturing with a needle.

The device according to the invention denies access to the piston and prevents the piston from being withdrawn. Indeed, in the device according to the invention, if any attempt is made at accessing the piston, an attempt is made to withdraw the actuating rod but, because of the shape of the central opening of the rigid cover which forms a means of stopping the actuating rod in the proximal direction, the actuating rod is halted by this rigid cover and the piston cannot be withdrawn. Furthermore, because of the presence of a stopper made of a material resistant to puncturing with a needle, access to the piston is impossible.

In this application, the distal end of a component is to be understood as meaning the end furthest from the user of the device and the proximal end is to be understood as meaning the end closest to the user of the device.

The plug is arranged to translate freely in the tubular body between the piston and the proximal end of the said body. In an embodiment of the invention, the actuating rod is fixed at its distal end to the plug. In another embodiment of the invention, the actuating rod is not fixed to the plug.

Advantageously, there is a bearing interface between the plug and the piston.

In one preferred embodiment of the invention, a means of stopping in the proximal direction is fixed to the actuating rod between the cover and the plug. The distal end of the actuating rod can be secured to the piston, for instance via the plug.

Advantageously, the plug and the piston are fixed in terms of translation, one on the other.

In one embodiment of the invention, the cover is made of aluminium and is crimped to the flange of the device.

In another embodiment of the invention, the cover is made of stainless steel and clipped in a definitive way to the flange.

In another embodiment of the invention, the cover is made of plastic.

In one embodiment of the invention, the cover is in the form of two halves of a ring, these being rigid and snap-fastened to one another, the two halves of the ring being able to be fixed to the flange, trapping it, each half if a ring comprising a lower platform comprising a semicircular opening corresponding to the external dimensions of the tubular body, and an upper platform comprising a semicircular opening designed for the passage of the actuating rod such that it is free in translational movement.

In one embodiment of the invention, the two halves of the ring are symmetric.

Advantageously, the means of snap-fastening one half of the ring into the other are situated inside each ring half. As a preference, the ring that results from the snap-fastening one inside the other of the two ring halves has on its exterior surface no snap-fastening or disengagement means.

The plug is made of a material resistant to puncturing with a needle. As a preference, the thickness and the nature of the material of the plug are chosen so that the plug cannot be punctured with a needle. As a preference, the material of which the plug is made is chosen from plastics, polyolefin polymers, polycarbonates and blends thereof.

Advantageously, the plug is connected to the distal end of the actuating rod by screwing or snap-fastening of the said rod into the plug.

In one embodiment of the invention, the plug is not secured to the piston.

In another embodiment of the invention, the plug is connected to the piston by screwing of the said plug into the piston.

In one embodiment of the invention, the actuating rod is equipped with at least one projection directed in a plane roughly radial with respect to the axis of the actuating rod, this projection being situated between the plug and the proximal end of the tubular body.

BRIEF DESCRIPTION OF THE DRAWINGS

The invention will be better understood from the description which follows, with reference to the attached drawing:

FIG. 8 is a perspective view of a cover according to FIG. 5, once closed.

DETAILED DESCRIPTION OF THE DRAWINGS

Figure 1:
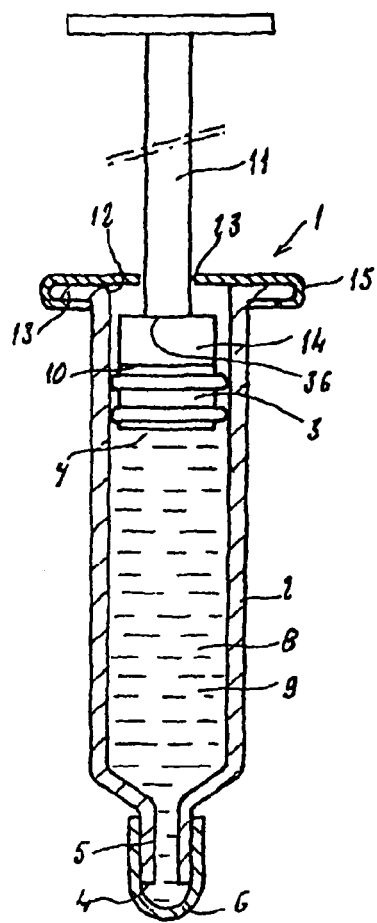
FIG. 1 is a view in section of a device according to a first alternative form of the invention, once filled.

FIG. 1 depicts a device 1 comprising a tubular body 2 made of glass and a piston 3 able to slide inside the tubular body. The tubular body 2 has, at its distal end 4, a tip 5 to take a needle, for example a hollow hypodermic needle (not depicted), this tip being closed by a cap 6, and, at its proximal end 12, a flange 13.

The lower end 7 of the piston defines inside the tubular body 2 an internal working volume 8 filled with a medicinal liquid 9. A plug 14, separate from the piston 3, is fixed to the distal end 36 of an actuating rod 11 protruding from the proximal end 12 of the tubular body 2. In a not depicted embodiment of the invention, the actuating rod 11 is not fixed to the plug 14. This plug 14 is arranged so that it is free to move in translation inside the body 2, on the proximal side of the said piston 3, bearing against the latter in the distal direction. There is therefore a bearing interface 10 between the plug 14 and the piston 3.

A rigid aluminium cover 15 is crimped onto the flange 13 and has a central opening 23 for the passage of the actuating rod 11 such that it is free in translation in the proximal direction.

Thus, during the process of manufacture of the device depicted in FIG. 1, if somebody attempts to withdraw the rod 11 that actuates the piston 3 from the tubular body after the step of filling the tubular body 2 but before the device is packaged, this will bring the plug 14 into contact with the rigid cover 15. This cover halts the plug 14 of the actuating rod 11 and therefore the actuating rod 11 itself. Thus, even if the actuating rod 11 is fully withdrawn from the tubular body 2, separating it from the plug 14, the latter remains inside the tubular body 2 and prevents subsequent access to the piston 3. Because of the presence of the plug 14, it is not possible to puncture the piston 3 by introducing a sharp means through the opening 23.

Figure 2:
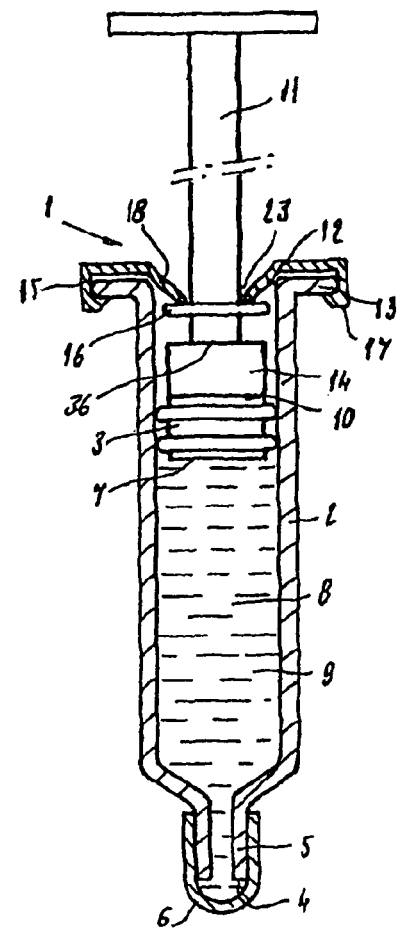
FIG. 2 is a view in section, once filled, according to a second alternative form.

FIG. 2 depicts another alternative form of a device according to the invention. The references that denote the same elements in FIGS. 1 and 2 are repeated. The actuating rod 11 is equipped with radial projections 16 situated facing each other on that part of the actuating rod that lies inside the tubular body 2. These projections 16 forming stop means can collaborate with the cover 15 to prevent the piston 3 from being moved towards the proximal end 12 of the tubular body beyond a predetermined limit.

According to this second alternative form of the invention, the cover 15 is made of stainless steel and is clipped in a definitive way onto the flange 13 using an annular collar 17. The cover 15 further comprises radial tabs 18 extending into the central opening 23 and capable of halting the translational movement, in the proximal direction, of the projections 16.

Figure 3:
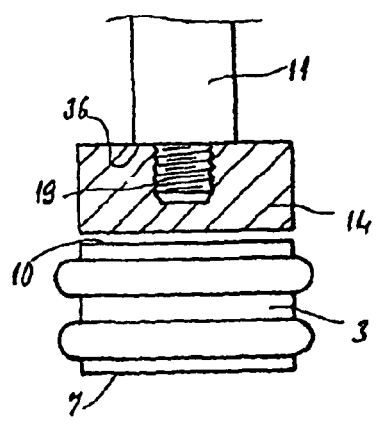
FIG. 3 is a part sectional view showing the connection between an actuating rod and a plug of a device according to the first alternative form depicted in FIG. 1.

FIG. 3 depicts an actuating rod 11 screwed using a screw or threaded part 19 into the plug 14. The piston 3 is not connected to the plug 14. According to this first alternative form of the invention, it is therefore not possible for the user to move the piston 3 towards the proximal end of the tubular body 2 of the syringe. Nor is it possible to access the piston 3, even if the actuating rod 11 is unscrewed, because of the presence of the plug 14 between the cover 15 and the piston 3.

Figure 4:
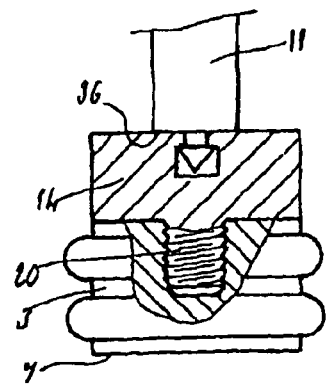
FIG. 4 is a part sectional view showing the connection between an actuating rod, a plug and a piston according to the second alternative form depicted in FIG. 2.

FIG. 4 depicts an actuating rod 11 fixed and clipped into the plug 14. According to this second alternative form of the invention, the plug 14 is screwed onto the piston 3 using a screw or threaded part 20. Thus, the distal end of the actuating rod 11 is secured to the piston 3 via the plug 14.

Figure 5:
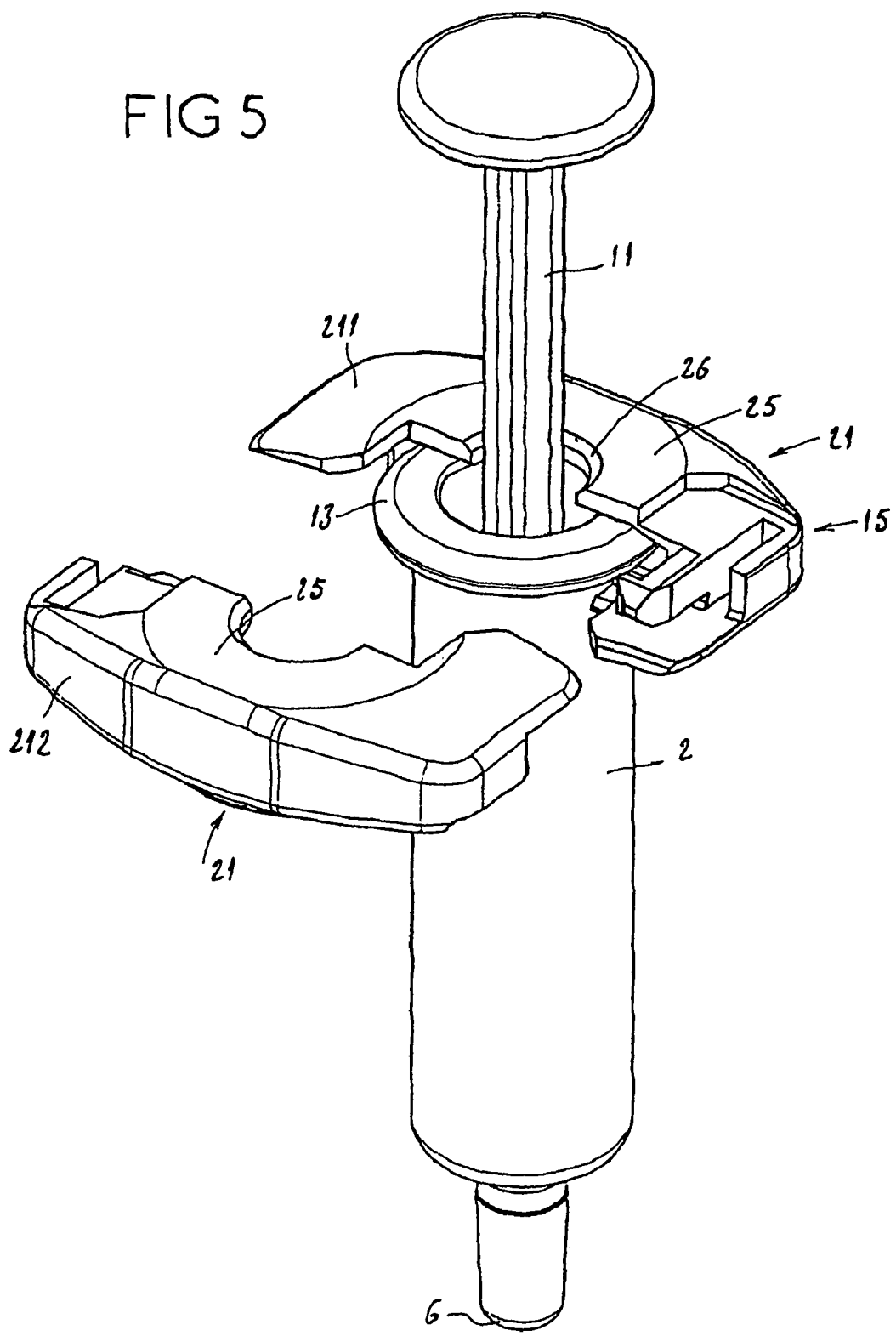
FIG. 5 is an exploded perspective view of a cover belonging to a third alternative form of a device according to the invention.

FIG. 5 depicts a cover 15 comprising a first half 211 of a ring 21 fixed to the flange 13 of the syringe and a second half 212 of a ring 21 ready to be clipped into the said first ring half 211.

Figure 6:
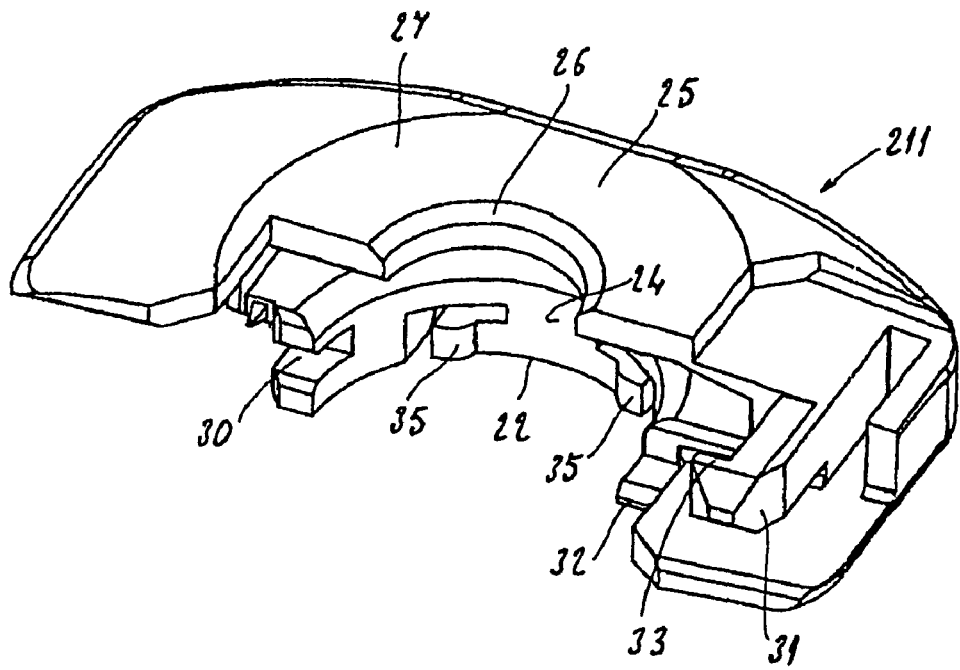
FIG. 6 is a perspective view from above of a half ring of a cover according to FIG. 5.

As can be seen in FIG. 6, the half 211 of the ring 21 comprises a lower platform 22 comprising a semicircular opening 24 corresponding to the external dimensions of the tubular body 2. This half 211 of the ring 21 also comprises an upper platform 25 comprising a semicircular opening 26 the dimensions of which allow the actuating rod 11 to pass such that it is free in translational movement. This upper platform 25 comprises a top face 27 and a bottom face 28.

Figure 7:
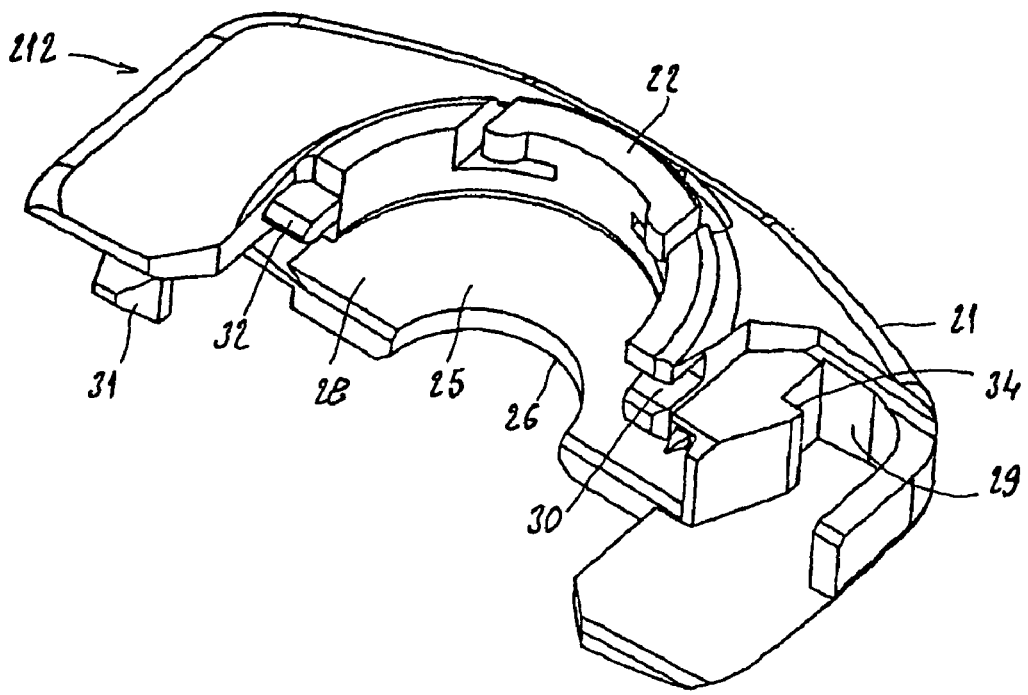
FIG. 7 is a perspective view from beneath of a half ring of a cover according to FIG. 5.

As is apparent from FIGS. 6 and 7, each half 211 or 212 of the ring 21 comprises, situated between its bottom platform 22 and its top platform 25, two distinct recesses 29 and 30 and, on the other side, two distinct studs 31 and 32. The stud 31 of a first half 211 of a ring 21 has a cutout 33 able to clip into a cutout 34 of the recess 29 of the second half 212 of the ring 21. The stud 32 of a first half 211 of the ring 21 is able to clip into the recess 30 of the second half 212 of the ring 21.

Each half 211 or 212 of the ring 21 also comprises two blocks 35 allowing the bottom platform 22 to be adjusted to suit the external dimensions of the tubular body 2 so as not to compromise the grip of the ring on the syringe.

FIG. 8 depicts the cover 15 of FIGS. 5 to 7 for which the two halves 211 and 212 of the ring 21 are clipped permanently together, around the tubular body 2 and on each side of the flange 13. Once the cover 15 is fixed permanently on the tubular body 2, it is impossible to access the interior of the said body without destroying this cover.

The present invention is not restricted to the embodiments described by way of example in this patent application.

The invention claimed is:

1. A tamper-evident syringe comprising:
   a tubular body with a longitudinal axis having a piston able to slide inside the tubular body and arranged in an initial position defining, with the tubular body, a reservoir for containing a liquid, the tubular body having a circumference;
   a rod for actuating the piston and extending beyond a proximal end of the body;
   a tip at a distal end of the body to accept a needle;
   a flange defined at the proximal end of the body; and
   tamper-evident means securable about an entire circumference of the flange, the tamper-evident means comprising:
      two separate pieces dimensioned for receiving the flange and an entire circumferential portion of the tubular body therebetween when the two separate pieces are permanently secured to each other about the longitudinal axis by at least one locking mechanism, so that the flange is maintained between the two pieces;
      a cover plate formed from the two separate pieces configured to cover the at least one locking mechanism when the two separate pieces are permanently secured to each other to prevent access to the locking mechanism;
      a lower platform formed from the two separate pieces defining a first opening having a first size and substantially circular shape and configured to receive the circumference of the tubular body, each of the two separate pieces forming a portion of the first opening, wherein each portion of the first opening is smaller than the flange; and
      an upper platform formed from the two separate pieces defining a second opening having a second size and substantially circular shape, each of the two separate pieces forming a portion of the second opening, wherein each portion of the second opening is smaller than the flange,
      wherein the first opening has a size and shape corresponding to the external dimensions of the body and the second opening has a size and shape to permit free movement of the rod therein and to prevent removal of the piston from the body.

2. The tamper-evident syringe according to claim 1, wherein the tamper-evident means is plastic.

3. The tamper-evident syringe according to claim 1, wherein each of the two pieces of the tamper-evident means are complementarily sized and shaped so as to be permanently securable together.

4. The tamper-evident syringe according to claim 1, wherein it further comprises a plug provided in the body at or near a proximal side of the piston, the plug being made of material resistant to puncturing with a needle and having means for coupling with the rod.

5. The tamper-evident syringe according to claim 1, further comprising means for preventing removal of the rod from the body, said means being provided on the rod between the tamper-evident means and a plug.

6. The tamper-evident syringe according to claim 1, wherein the two pieces of the tamper-evident means are configured to be securable about the circumference of the flange substantially perpendicular to an axis of the tubular body.

7. The tamper-evident syringe according to claim 6, wherein each of the two pieces comprises substantially half of the first opening, the first opening being substantially circular when the tamper evident means are secured about the circumference of the flange.

* * * * *